US00PP14066P39

(12) United States Plant Patent
Moser

(10) Patent No.: US PP14,066 P3
(45) Date of Patent: Aug. 19, 2003

(54) CHRYSANTHEMUM PLANT NAMED 'MOZA PA 01'

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 20 days.

(21) Appl. No.: 09/864,900

(22) Filed: May 24, 2001

(65) Prior Publication Data

US 2002/0188978 P1 Dec. 12, 2002

(51) Int. Cl.[7] ..... A01H 5/00
(52) U.S. Cl. ..... Plt./289
(58) Field of Search ..... Plt./289

(56) References Cited

U.S. PATENT DOCUMENTS

PP9,919 P * 6/1997 Wain ..... Plt./269
PP10,463 P 6/1998 Wain ..... Plt./289

* cited by examiner

*Primary Examiner*—Bruce R. Campell
*Assistant Examiner*—Anne Marie Grünberg
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, vigorous growth habit, and consistent natural season flowering habit during late September.

1 Drawing Sheet

LATIN NAME OF THE GENUS AND SPECIES OF THE PLANT CLAIMED

*Chrysanthemum morifolium.*

VARIETY DENOMINATION

'MOZA PA 01'.

BACKGROUND OF THE INVENTION

The present invention relates to a new and distinct cultivar of Chrysanthemum plant, herein after referred to by the cultivar name 'MOZA PA 01 .'

This new cultivar originated from hybridization of a female parent Chrysanthemum cultivar (unpatented in the United States) with a male parent Chrysanthemum cultivar (unpatented in the United States). The new cultivar was discovered by the inventor in November 1998.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'MOZA PA 01' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'MOZA PA 01.' These characteristics in combination distinguish 'MOZA PA 01' as a new and distinct Chrysanthemum:

1. Decorative type inflorescence;
2. Consistent flowering response to short days, blooming consistently after 49 days of short day length;
3. Vigorous growth habit; and
4. Consistent natural season flowering habit during late September.

Plants of the new cultivar are similar to plants of the female parent cultivar in most horticultural characteristics, however plants of the new cultivar differed from plants of the female parent cultivar in the following characteristics:

1. The new cultivar has different color ray florets;
2. The new cultivar has a larger diameter bloom;
3. The new cultivar is shorter; and
4. The new cultivar has a more flexible plant shape (A flexible plant habit refers to the plant's lack of brittleness. The plant resists breaking with wind and overhead water).

Plants of the new cultivar are similar to plants of the male parent cultivar in most horticultural characteristics, however plants of the new cultivar differed from plants of the male parent cultivar in the following characteristics:

1. The new cultivar is taller; and
2. The new cultivar naturally blooms 2 weeks later.

Plants of the new cultivar are similar to plants of the commercial cultivar 'CLEAGAR GF1' (disclosed in U.S. Plant Pat. No. 10,463) in most horticultural characteristics, however plants of the new cultivar differed from plants of the commercial cultivar in the following characteristics:

1. The new cultivar has larger diameter blooms;
2. The new cultivar has more blooms per flowering branch;
3. The new cultivar is taller and wider; and
4. The new cultivar has a more flexible plant habit.

BRIEF DESCRIPTION OF THE PHOTOGRAPHS

The photograph shows a plant of the new cultivar grown in a 1-gallon container. A single cutting was propagated in the container.

DETAILED BOTANICAL DESCRIPTION

In the following description, color references are made to The Royal Horticultural Society Colour Chart except where general terms of ordinary dictionary significance are used. The following observations and measurements describe approximately 85 day old plants grown in a commercial field on Oxnard, Calif. in the month of September 2000. The growing conditions range from 60° to 65° F. at night to 70° to 85° during the day. Measurements and numerical values represent averages of typical flowering types.

Botanical classification: *Chrysanthemum morifolium* cultivar 'MOZA PA 01'.
Commercial classification: Garden-type Chrysanthemum.
Parentage: Hybridization of female parent Chrysanthemum cultivar MZ 282-01 (unpatented in the United States, and undistributed commercially) with a male, parent Chrysanthemum cultivar MZ 365-01 (unpatented in the United States, and undistributed commercially).

PROPAGATION

Time to rooting: 7 to 14 days at approximately 21° C.
Rooting habit: Fine, fibrous.

PLANT

Growth habit: Mounding herbaceous perennial.
Height: Approximately 25 cm.
Branching characteristics: Free Branching.
Length of Lateral Branches: Approximately 20 cm.
Number of leaves per lateral branch: Approximately 21.

FOLIAGE

Leaf:
*Arrangement*.—Alternate.
*Average length*.—Approximately 6.4 cm.
*Average width*.—Approximately 4.0 cm.
*Shape of blade*.—Ovate.
*Apex*.—Acuminate.
*Base*.—Attenuate.
*Attachment*.—Stalked.
*Margin*.—Serrate.
*Texture of top surface*.—Lightly pubescent.
*Texture of bottom surface*.—Lightly pubescent.
*Color*.—Young foliage upper side: Near 137B. Young foliage under side: Near 137B. Mature foliage upper side: Near 137A. Mature foliage under side: Near 137A. Venation upper side: Near 138C. Venation under side: Near 138C.

Petiole:
*Petiole color*.—Approximately 137B.

BLOOM

Inflorescence:
*Flowering habit*.—Induced by darkness period greater than 13.5 hours, blooms consistently after 49 days of appropriate day length required to induce and develop blooms.
*Inflorescence form*.—Decorative.
*Natural flowering season*.—Approximately mid-September.
*Number of inflorescences per stem*.—Approximately 16.
*Inflorescence diameter*.—Approximately 4.5 cm.
*Inflorescence depth*.—Approximately 1.2 cm.
*Inflorescence longevity on plant*.—Approximately 21–29 days.
*Persistence*.—Persistent.
*Fragrance*.—Not present.

Ray florets:
*Texture*.—Shiny.
*Average number per flower*.—Approximately 140.
*Shape*.—Oblanceolate.
*Margin*.—Entire.
*Apex*.—Obtuse.
*Length*.—Approximately 2.0 cm.
*Width*.—Approximately 0.4 cm.
*Color*.—Upper surface at first opening: Near 6C. Upper surface at maturity: Near 6A. Upper surface at fading: Near 7B. Under surface at first opening: Near 6C. Under surface at maturity: Near 6A. Under surface at fading: Near 7B.

Disc florets:
*Appearance*.—Shiny.
*Texture*.—Smooth.
*Average number per flower*.—Approximately 30.
*Shape*.—Cylindric.
*Apex*.—Obtuse.
*Average length*.—Approximately 0.5 cm.
*Average width*.—Approximately 0.3 cm.
*Color*.—At first opening: Near 144B. At maturity: Near 144A. At fading: Near 143C.

Peduncle:
*Length*.—At terminal end (shortest): Approximately 3 cm. At lateral end (longest): Approximately 6.54 cm.
*Strength*.—Moderate.
*Color*.—Near 144A.
*Habit*.—Erect.

Inflorescence bud:
*Length*.—Approximately 0.3 cm.
*Diameter*.—Approximately 0.4 cm.
*Form*.—Globular.
*Color*.—Near 147B.

Sepals:
*Appearance*.—Matte.
*Texture*.—Lightly pubescent.
*Number*.—Approximately 24.
*Shape*.—Ovate.
*Margin*.—Entire.
*Apex*.—Acute.
*Color*.—Upper side: Near 137A. Upper side: Near 137B.

REPRODUCTIVE ORGANS

Ray florets: Pistillate:
*Number of pistils perfloret*.—1.
*Stigma shape*.—2 branched.
*Stigma color*.—Near 5A.
*Style color*.—Near 5A.
*Style length*.—Approximately 0.3 cm.
*Number of stamens per floret*.—Absent.

Disc florets:
*Number of pistils per floret*.—1.
*Stigma shape*.—Cylindric.
*Stigma color*.—Approximately 1A.
*Style length*.—Approximately 0.3 cm.
*Style color*.—Approximately 1C.
*Number of stamens per floret*.—Approximately 5.
*Anther shape*.—Tubular.
*Anther color*.—Near 16A.
*Pollen color*.—Near 17B.

OTHER CHARACTERISTICS

Seed production: Commercially, this plant is not used or observed in a stage wherein seeds would be produced. Therefore, seed production has not been observed.
Disease resistance: Neither resistance nor susceptibility to diseases and pests have been observed in this cultivar.

What is claimed is:

1. A new and distinct variety of Chrysanthemum plant named 'MOZA PA 01' as herein illustrated and described.

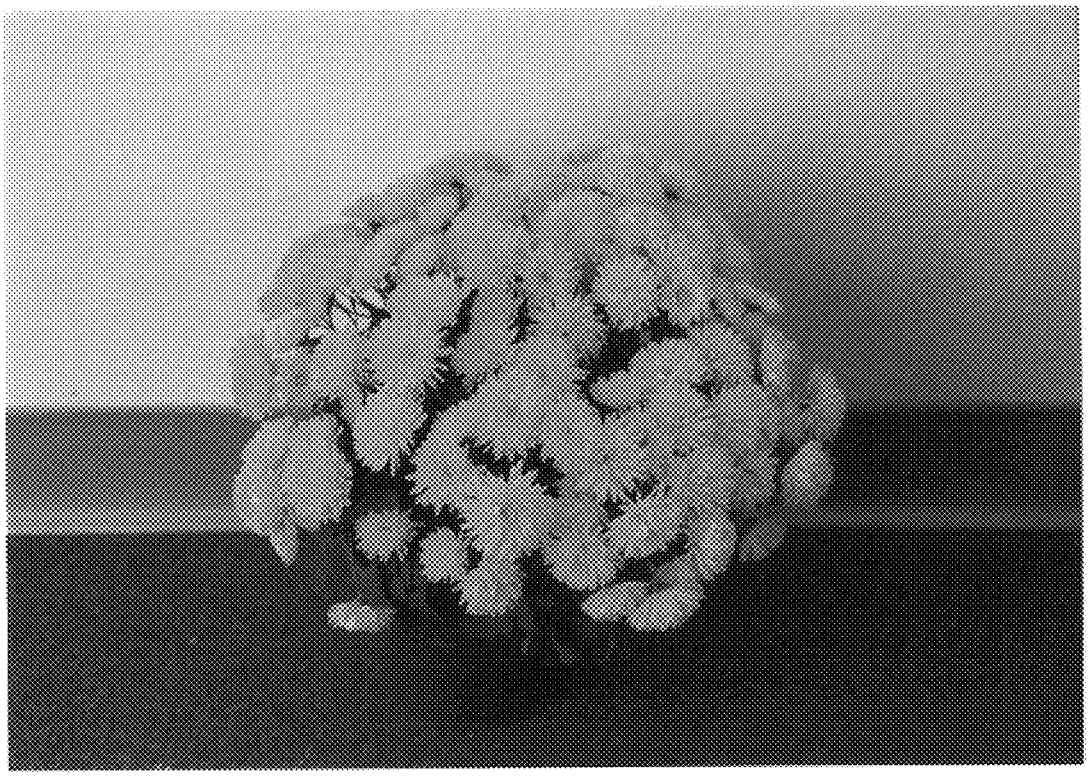

* * * * *